United States Patent [19]

Kloth

[11] Patent Number: 5,285,253
[45] Date of Patent: Feb. 8, 1994

[54] CUVETTE FOR HOLDING SUBSTANCES TO BE ANALYZED BY OPTICAL MEANS

[76] Inventor: Bernd Kloth, Müssenredder 8, D-2000 Hamburg 65, Fed. Rep. of Germany

[21] Appl. No.: 920,297

[22] PCT Filed: Aug. 16, 1991

[86] PCT No.: PCT/EP91/01564
§ 371 Date: Aug. 14, 1992
§ 102(e) Date: Aug. 14, 1992

[87] PCT Pub. No.: WO92/11527
PCT Pub. Date: Jul. 9, 1992

[30] Foreign Application Priority Data

Dec. 17, 1990 [DE] Fed. Rep. of Germany ... 9016832[U]

[51] Int. Cl.$^5$ .......................... G01N 1/10; B01L 9/00
[52] U.S. Cl. .................................. 356/246; 250/576; 422/102; 422/104
[58] Field of Search ............... 356/244, 246, 440, 427, 356/428; 250/576; 422/102, 104; 215/247; 436/172, 165, 180, 809

[56] References Cited

U.S. PATENT DOCUMENTS

| | | | |
|---|---|---|---|
| 3,607,098 | 9/1971 | Strande | 356/246 |
| 4,643,033 | 2/1987 | Solazzi | 356/246 |
| 4,761,378 | 8/1988 | Godsey | 422/102 |
| 4,799,599 | 1/1989 | Hermann | 356/246 |
| 5,035,866 | 7/1991 | Wannlund | 356/246 |

Primary Examiner—Richard A. Rosenberger
Assistant Examiner—Hoa Q. Pham
Attorney, Agent, or Firm—Fliesler, Dubb, Meyer & Lovejoy

[57] ABSTRACT

In order to ensure that, in a cuvette for holding substances to be analyzed preferably by optical means, more particularly for the analysis of chromogenic substances, solutions and substrates, having a measuring section that is closed at the bottom for accommodating the substance, that, when providing optimal marginal conditions for the measurement, the handling of the cuvette prior to, during and subsequent to the termination of the measurement operations, can take place with a minimal risk of contamination, it is proposed that, to the measuring section, a section extending the cuvette adjoins, with the aid of which a preferably detachable plug-in connection can be established to the measuring section of a further cuvette.

30 Claims, 7 Drawing Sheets

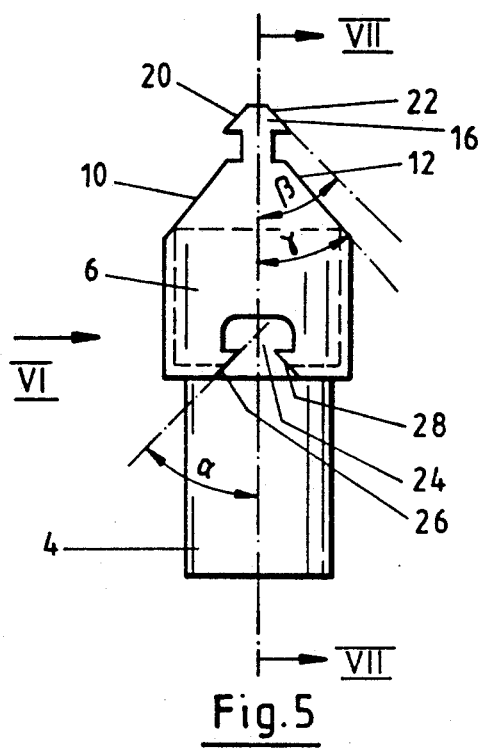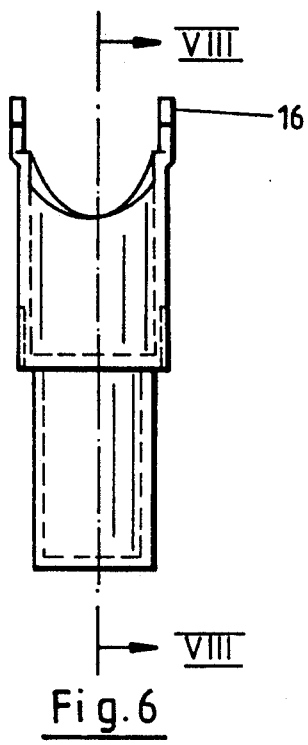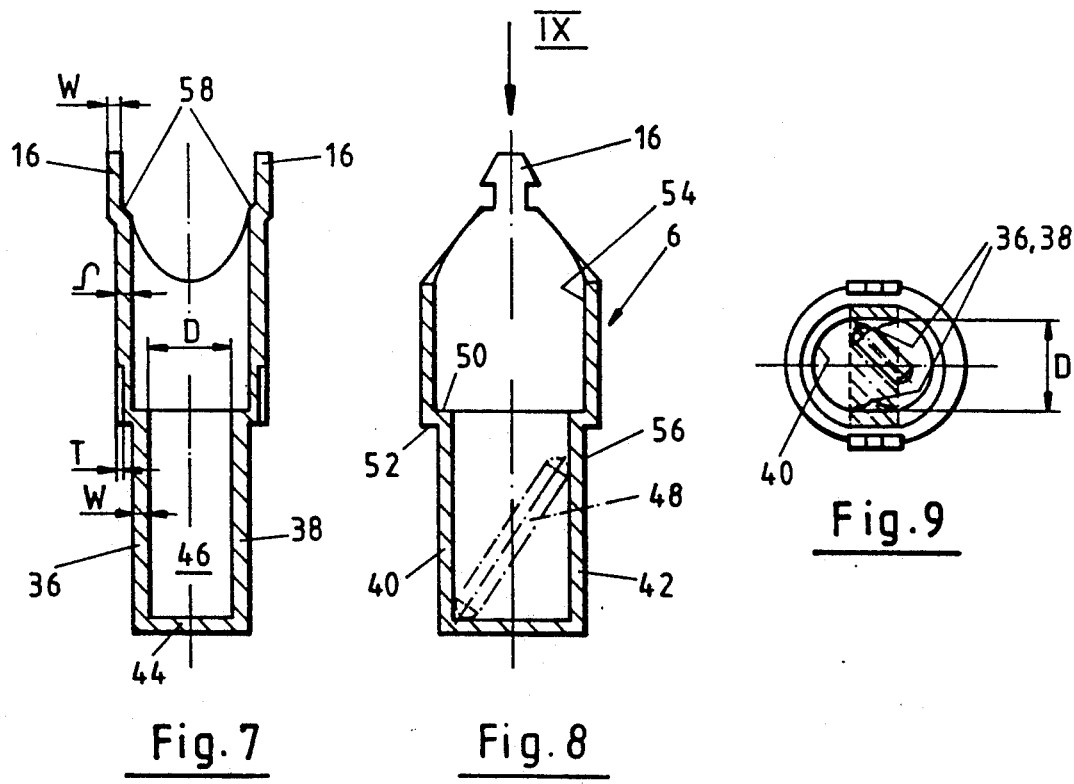

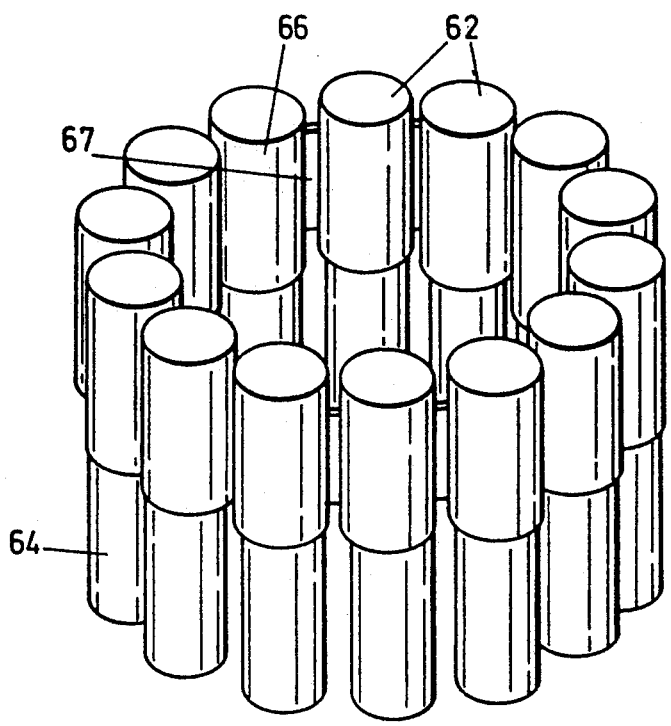
Fig. 10
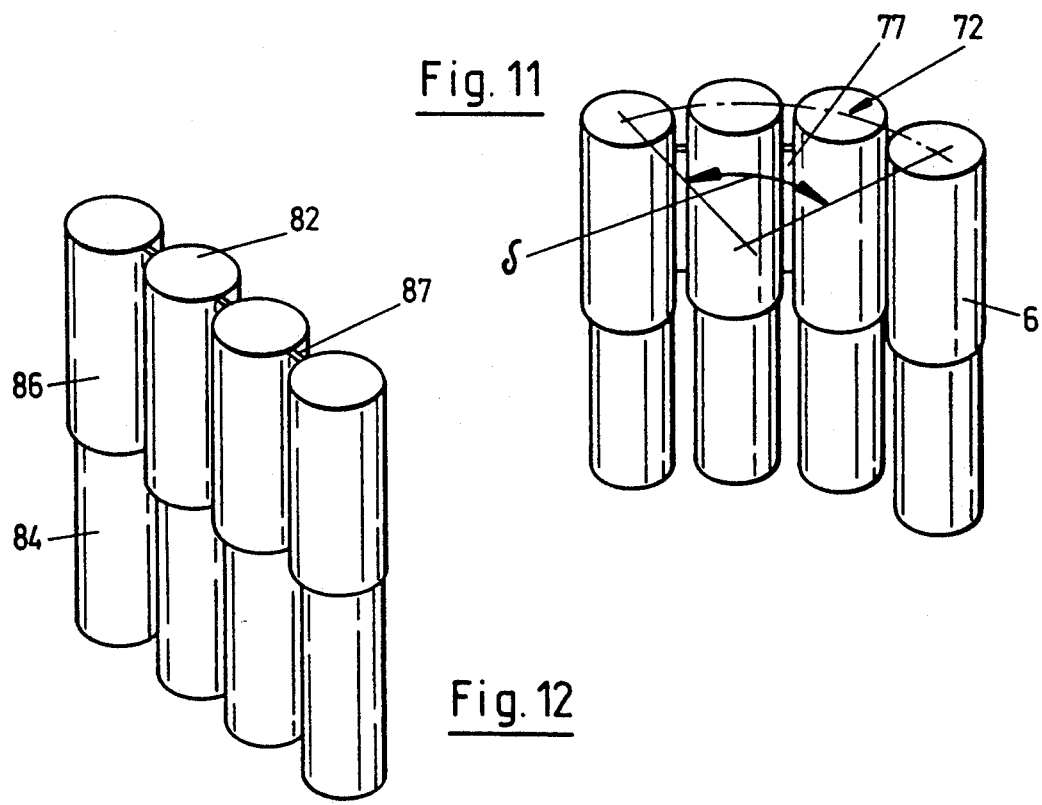
Fig. 11
Fig. 12

CUVETTE FOR HOLDING SUBSTANCES TO BE ANALYZED BY OPTICAL MEANS

SCOPE OF APPLICATION

The present invention relates to a cuvette for holding substances to be analyzed preferably by optical means, more particularly a measuring cuvette for analyzing chromogenic substances, solutions or substrates. In this cuvette, a special suitability is provided for the analysis of photometric determinations over the entire spectral range, in this case especially of chromogenic substrates, enzyme-kinetic determinations and end-point determinations; however, the cuvette may be employed anywhere it is intended to transport, store and/or supply to an analyzer a substance to be analyzed.

STATE OF THE ART

The invention proceeds from a cuvette for holding substances to be analyzed preferably by optical means, more particularly for the analysis of chromogenic substances, solutions and substrates, having a measuring section that is closed at the bottom for holding the substance.

Such so-called optical measuring cuvettes are employed by preference for analytical measurements of enzymatic tests and coagulation end-point determinations in accordance with the so-called fibrin timer measurement principle or else in enzyme kinetics analyses. In measurements of this kind, the measuring cuvette, for the measuring operation, is placed into a measuring block or measuring rotor, in which case, with the aid of a stirring rod placed on the bottom of the measuring section of the cuvette, an as homogeneous as possible a mixing of the substances to be analyzed and, simultaneously or subsequently, the actual measuring operation is effected. After the completion of the measurements, the measuring cuvette is removed from the measuring block or rotor. When this is done, it has to be ensured that the risk of contamination for the operators, e.g. by infected specimen material, is kept as low as possible.

SUMMARY OF THE INVENTION

That is why the invention is based upon the technical problem of making sure by means of simple steps that, by the provision of optimal marginal conditions for the measurement, the handling of the cuvette prior to, during and subsequent to the completion of the measurements, can take place involving a minimal risk of contamination.

According to the invention, a cuvette is provided which is of such a design that it can be had recourse to for accommodating the measuring specimen and to serve at the same time as an empty cuvette and, on the one hand, for screening off the measuring section and, with it, the substance to be analyzed from the outside and, on the other, for serving as a handling or transporting aid for the measuring cuvette containing the substance to be analyzed. For this purpose it is only necessary to insert two identically configured cuvettes into each other, whereby, owing to the attached or inserted empty measuring cuvette, a closure of the measuring space of the other measuring cuvette is brought about. In this state it is possible for the measuring specimen, by way of example, infected specimen material, to be removed from the measuring block or from a rotor provided for this without the involvement of any risk of contamination for the operators. Consequently, also the disposal of the analyzed specimens is without problems. Especially when the plug-in connection between the cuvettes is designed so as to be detachable, a simplification of the method steps in the disposal of the specimens results since it is possible for the plug-in connection to be disengaged already prior to the actual disposal method steps being performed. In this connection, due to the steps according to the invention, the additional advantage is obtained that empty cuvettes can, on the one hand, be stacked or transported in a space-saving manner so that a stirring rod always placed in the measuring cuvette cannot be lost. The cuvettes stacked in this way can be introduced into an individual cuvette dispenser, from which an individual removal of the cuvettes is rendered possible with the risk of contamination of the measuring section being reduced to an absolute minimum.

It is generally possible to extend the cuvette in the upward direction, i.e. adjoining to the measuring section, or in the downward direction, i.e. adjoining to the measuring section bottom. In the latter case it is possible to construct the extension section so as to be either wider or more slender than the outer dimension of the actual measuring section.

CONSTRUCTIONS AND FURTHER DEVELOPMENTS

It is true that the further development according to the invention has proved to be particularly advantageous with regard to the handling of the cuvette, according to which the extension section extends the cuvette in the upward direction and possesses an internal contour which corresponds essentially to the external contour of the measuring section. By means of this construction the distance between the substrate to be analyzed and the rim of the cuvette which is open towards the top is kept as great as possible so that an escape to the outside of the substrate is effectively precluded, especially when the measuring section of the one cuvette is covered by the measuring section of the attached cuvette. When the plug-in connection is secured by an additional locking means, by way of example, in the form of a snap-action locking means, this construction opens up the possibility of employing kinematics for the stirring of the substance in the measuring block or rotor that had not been employable up till now, whereby the quality of the measurement can be additionally increased. By adapting the internal contour of the extension section to the external contour of the measuring section, a positive engagement of the measuring cuvettes results, due to which it is possible to improve not only the stackability, but also the sealing of the measuring substance against the outside.

The measuring cuvette according to the invention is accordingly constructed in two parts. In case the two sections of the cuvette merge into each other inside and/or outside by means of a shoulder, in the inserted-into-each-other state of the two cuvettes, at least one additional sealing or functional surface is provided, with the aid of which the substance to be measured in the inserted-into-each-other state of two cuvettes is screened off from the outside or an additional stabilization of the two inserted-into-each-other cuvettes relative to each other can be ensured.

At the end, the extension section is preferably provided with at least one locking part which can be brought into locking engagement with a complementarily constructed locking section that is axially offset hereto on the further cuvette entering into plug-in connection. With this construction is it successfully accomplished to establish a secure locking by means of a single translatory relative motion between the two cuvettes to be interconnected. The removal of the measuring cuvette from a measuring block or rotor can be effected in this manner in that an empty cuvette is pressed upon the measuring cuvette, whereby, solely by the axial movement of the empty cuvette, a sufficiently secure plug-in connection is provided.

Accordingly, the measuring cuvette can be removed from the measuring block without being touched, which helps to significantly reduce the risk of a contamination by possibly infected measuring substances or measuring substrates.

The locking between the fitted-together cuvettes may be effected in the most widely varied ways. It is thus conceivable, for instance, to provide a frictional connection within the area of the fitted-together areas. It is true that a locking has proved to be particularly advantageous in which a positive interlocking and, preferably, a locking engagement of locking elements takes place. This type of locking offers the special advantage that the function of the locking becomes very largely independent of the tolerances in the manufacture of the cuvettes.

When, according to the invention, positioning surfaces are additionally provided within the area of the locking means, then these may be advantageously utilized for the reciprocal alignment of the cuvettes to be inserted into each other. This opens up in an advantageous manner the possibility of stacking the measuring cuvettes, e.g. in a dispenser in such a way that an easy separation and individual removal of the cuvettes is possible.

Especially when two positioning surfaces are allocated to the locking part according to the invention which taper in a wedge-shaped fashion towards each other, when the opposing surfaces arew pertinently constructed, an automatic positional fixation results within the locking section when the cuvettes are inserted into each other, so that it is possible to form a stack of measuring cuvettes which are oriented in exact alignment with each other.

Generally, if the cuvette is expediently designed, already a single locking part will suffice. However, in order to additionally increase the locking safety in the fitted-together state, according to the invention it has to be preferred to operate with several, by preference, two locking parts disposed spaced apart at a uniform circumferential distance.

When constructing the locking parts in the form of axially aligned hook sections with a correspondingly thin-walled construction of the measuring cuvette, an adequate radial elasticity is produced which can be utilized in an advantageous manner for selectively disengaging the, in the fitted-together state, snap-action latching means.

Preferably the hook sections have a thickness which corresponds essentially to the wall thickness of the cuvette within the area of the extension section.

Especially in interaction with the axially oriented hook sections of the locking parts the further development according to the invention is of particular advantage. According to this construction, within the area of the locking sections, only depressions, i.e. groove-like recesses, have to be provided for the corresponding hook sections, in which case already a very small depth of these recessed portions suffices for putting up an adequately strong resistance to the hook section subsequent to the gripping behind of the contour of the recessed portion. These recesses are very simple to realize when, for example, the cuvette is fabricated from plastic. In addition, this construction possesses the further advantage that the internal surface area of the cuvette can be constructed so as to be smooth all the way.

As already mentioned in the foregoing, for the simplification of the construction of the interlocking it is of advantage to construct the cuvette, at least within the area of the locking parts and/or of the locking sections, so as to be radially elastic. It suffices in this case to squeeze the cuvette together between index finger and thumb in order to disengage the hook sections for unlocking from the recesses.

The construction of the measuring cuvette according to the invention does, however, not limit the possibilities regarding the design of the measuring section. It is consequently possible to construct the cuvette in an advantageous manner at least within the area of the measuring section having an internal cross-section diverging from the circular shape, which is subsequently adapted to the optical measuring principle being employed in each case. By way of example, in order to be able to perform photometric tests in accordance with Lambert's law, the measuring cuvette according to the advantageous further development as per the invention, is constructed within the measuring area in such a way that, by means of the plane parallel side wall sections, it encloses a predetermined measuring layer thickness. Such photometric tests are conducted particularly in the analysis of chromogenic substrates and in enzyme kinetics. In order to falsify the measurement results as little as possible, it will have to be ensured that the plane parallel window for enclosing the measuring layer is executed so as to be as clear or as transparent as possible. It has been shown that plastics can be readily employed for this. Within this area, the use of polystyrenes and polymethylacrylates has proved to be especially advantageous, in which connection, the latter group, especially polymethylmethacrylate (PMMA) has ensured particularly good results. Over and above that, these plastics render possible such a precise processing, e.g. in the forming or moulding forming process, that the wall thicknesses of the measuring cuvette and the geometries of the cuvette cross-sections can be so exactly adhered to that reproducible measurements of high quality can be carried out. It is possible to adhere to these above-mentioned accuracies of shape even when the wall thickness of the cuvette and, with it, the thickness of the plane parallel side wall sections lie within the range of between 0.5 and 0.7 mm. By preference, in this case, the lateral distance of the plane parallel side wall sections and, with it, the dimensions of the measuring layer subjected to the optical measurement, is maintained within a range of between 5 and 10 mm. In addition, owing to the connection of the plane parallel side wall sections by means of rounded sections, the further advantage results that the substrate trapped in the measuring section and due to be analyzed can be subjected to an effective, thorough mixing when the cuvette is e.g. placed in a suitable rotor or vibrator. It is possible to additionally improve the thorough mixing by placing a stirring rod in the measuring cuvette. Especially when, according to the claim 21, the bottom of the measuring section is constructed so as to be even and plane, it is possible for the stirring rod to move gently and smoothly in the measuring section when the measuring cuvette is subjected to an appropriate motion, by way of example, to a rotation. Dead spaces in the measuring section are reliably avoided in this way, a circumstance from which the quality of the measuring results benefits additionally.

It is generally possible to construct the measuring section and the extension section in two parts. It is true that advantages with respect to the handling and cleaning or the sterilization of already used measuring cuvettes result when the cuvette is constructed overall of one piece.

The construction according to the invention even permits the combination of several cuvettes into measuring cuvette arrays or arrangements which are subsequently, in the form of a group, inserted into a measuring block or, to begin with, into a suitable mixing means or mixing rotor. In this case, adjacent measuring cuvettes are interconnected preferably by means of webs that have been formed on in one piece. When this is done, the position of the webs is preferably disposed in such a way that the elasticity of the cuvette which is necessary for establishing the interlocking between cuvettes that have been inserted into each other is impaired as little as possible.

In this manner it is possible to combine cuvettes so as to form segments, strips or closed rings or rotors which can be by and large inserted into each other to constitute appropriately configured cuvette arrays and which are capable of being preferably interlocked or brought into locking engagement.

According to a preferred further development, provision is made for effecting the array of several cuvettes by the cuvettes being disposed in a rotor that is constructed in the form of an annular disk in which receiving perforations are constructed, in which case one cuvette at a time is insertable with its measuring section into a receiving perforation, provision having preferably been made in this connection for two receiving perforations in each case to be parallely disposed.

BRIEF DESCRIPTION OF THE DRAWINGS

In the following several embodiment examples of the invention will be explained in greater detail with the aid of diagrammatical drawings. Thus

FIG. 5 shows a side elevation of the measuring cuvette;

FIG. 6 shows a view of the measuring cuvette with a line of vision according to arrow VI in FIG. 5;

FIG. 7 shows the section in the direction of VII—VII in FIG. 5;

FIG. 8 shows the section in the direction of VIII—VIII in FIG. 6;

FIG. 9 shows a view in the direction of IX in FIG. 8;

FIG. 10 is a representation of an arrangement of cuvettes interconnected by web structures in a circular format.

FIG. 11 is a representation of an arrangement of cuvettes interconnected by a web structure in an arcuate format.

FIG. 12 is a representation of an arrangement of cuvettes interconnected by a web structure in a linear format.

DETAILED DESCRIPTION OF THE INVENTION AND BEST WAY OF REALIZING THE SAME

Figure 1:
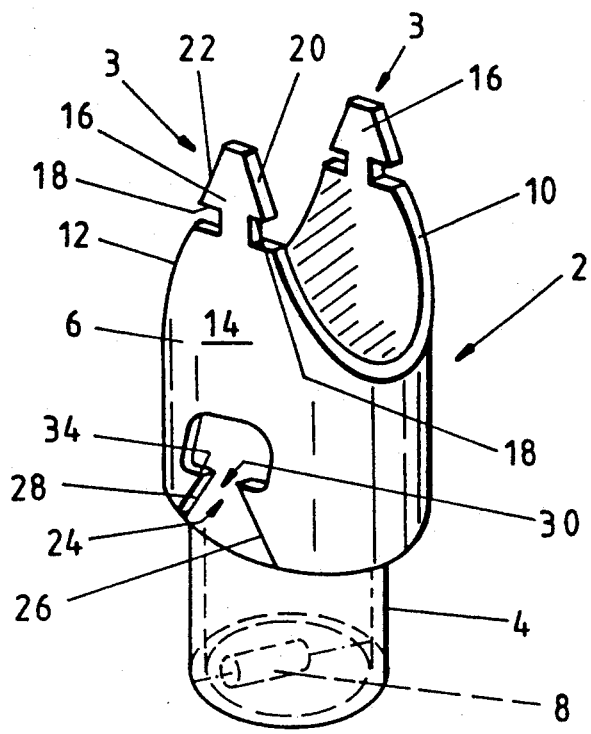
FIG. 1 shows a perspective view of a first embodiment of the measuring cuvette.
Figure 2:
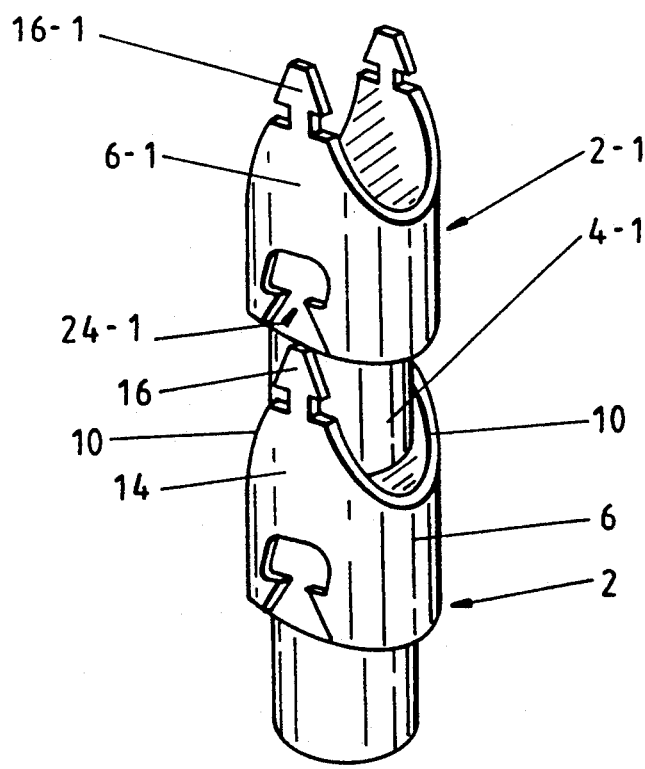
FIG. 2 shows a perspective view of two identically constructed measuring cuvettes in an axially aligned relative position prior to their being inserted into each other.

In the FIG. 1, with the reference number 1, a measuring cuvette is shown as is preferably employed in analytical measurements of enzymatic tests and coagulation end-point determinations according to the fibrin timer measuring principle. In this case it is a matter of an optical analysis of chromogenic substrates. It is true that these measuring cuvettes are also generally employed in enzyme kinetics, in which, in this case, an analysis of the substrate is likewise carried out by optical means.

Such measuring cuvettes are first of all inserted into a mixing means or mixing rotor in which a homogeneous thorough mixing of the substrate to be analyzed is carried out. The actual measuring process takes place subsequent to this. Finally, the measuring cuvette has to be removed from the measuring block or rotor in such a way that the risk of a contamination of the operators, e.g. by infected specimen material, can be kept to an absolute minimum. To this end the measuring cuvette is constructed as will be detailed in hereinafter.

To the actual measuring section 4 intended to hold the substrates or substances to be analyzed, an extension section 6 adjoins at the top which is constructed so as to be wider than the measuring section 4 and is constructed in such a way that it is capable of accommodating a measuring section 4-1 of an adjacent measuring cuvette. The disposition is such that a preferably detachable plug-in type connection between the adjacent cuvettes 2 and 2-1 can be established, in which the measuring section 4-1 of the inserted cuvette 2-1 very largely closes the measuring section 4 of the other measuring cuvette 2 in the upward direction and, in the inserted state, serves as a handling aid or transporting means for the measuring cuvette 2. Two main functions are provided by this:

a) The measuring cuvettes 2, 2-1, ..., 2-n are stackable in a space-saving manner, in which case, due to the plug-in connection, it has been reliably ensured that a stirring rod 8 accommodated in the measuring section 4, which at the same time serves as stirring section, cannot be lost;

b) When a measuring cuvette, after the stirring operation has been carried out, is to be removed from a measuring block or mixer or rotor, an empty cuvette may be had recourse to as a handle or handling means for the measuring cuvette holding the material to be measured, whereby a risk of contamination for the operators by possibly infected measuring substrate is ruled out from the outset;

c) When the measuring cuvettes are inserted into each other, the contour located above the measuring sections serves to ensure a scratch-proof storage of the cuvette. Scratch marks on the measuring window produce incorrect measurements.

In order to optimally do justice to these three basic functions, the measuring cuvette, according to a first embodiment as per FIGS. 2 to 9, is constructed as described below.

In order to facilitate the introduction of a measuring section 4-1 of a measuring cuvette 2-1 into the extension section 6 of the measuring cuvette 2, a clearance fit between the internal contour of the extension section 6 and the external contour of the measuring section 4-1 is provided. For the additional facilitation of the combination, the extension section 6 or 6-1 is provided with bevels 10 and 12 on two diametrically opposed sides. Between these bevels or chamfers 10 and 12 remain sections 14 which, on their ends, bear axially aligned hook sections 16 which serve as locking parts 3.

In the concrete case these hook sections are constituted of arrow-like configured double hooks which have two locking shoulders 18, which are in each case adjoined by a positioning surface 20 or 22. The positioning surfaces 20,22 taper towards each other and, in this way, define the arrow-shaped double hook which is able to enter into operational engagement with a locking section 24-1 to be described in greater detail hereinafter at the bottom end of the extension section 6-1 of the measuring cuvette 2-1. It becomes apparent from the illustrations as per FIGS. 2 to 4 that the locking sections 24 are axially aligned with the hook sections 16 so that the fitting together by insertion of second cuvettes 2,2-1 is only possible in a predetermined relative torsional position of the measuring cuvettes relative to each other.

The locking section 24 is constructed in the form of a recess or depression in the outer surface of the external section 6. The recess 24,24-1 possesses essentially the contour of a key hole, with two sections resulting in the process. Within the lower area, two chamfers 26,28 that taper angularly towards each other are formed, the inclination of the chamfers corresponds substantially to the slope of the positioning surfaces 20,22. The chamfers terminate in a construction 30, which is adjoined by an undercut round recess portion 32 with level retaining areas 34. With this construction it is possible to realize the following operations.

Figure 3:
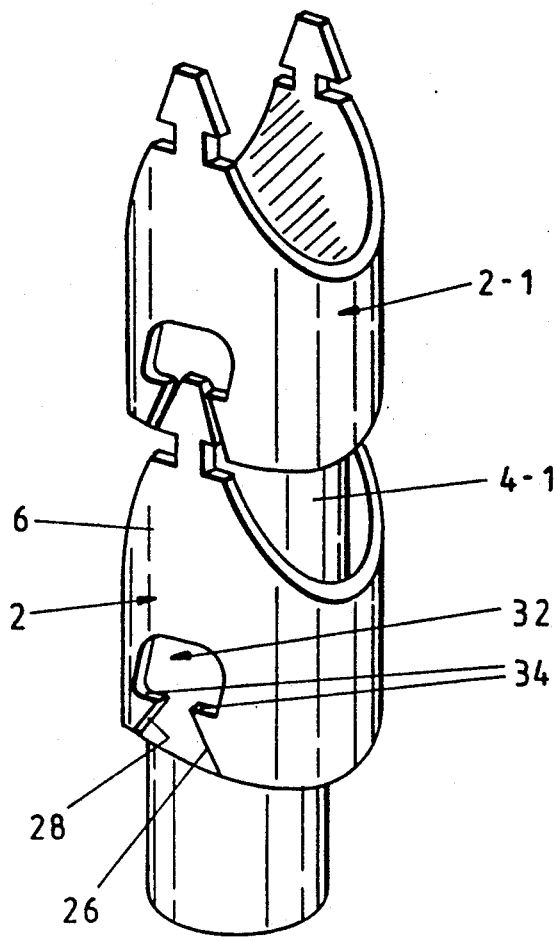
FIG. 3 shows the perspective view according to FIG. 2 in the loosely fitted-together state of the two cuvettes.
Figure 4:
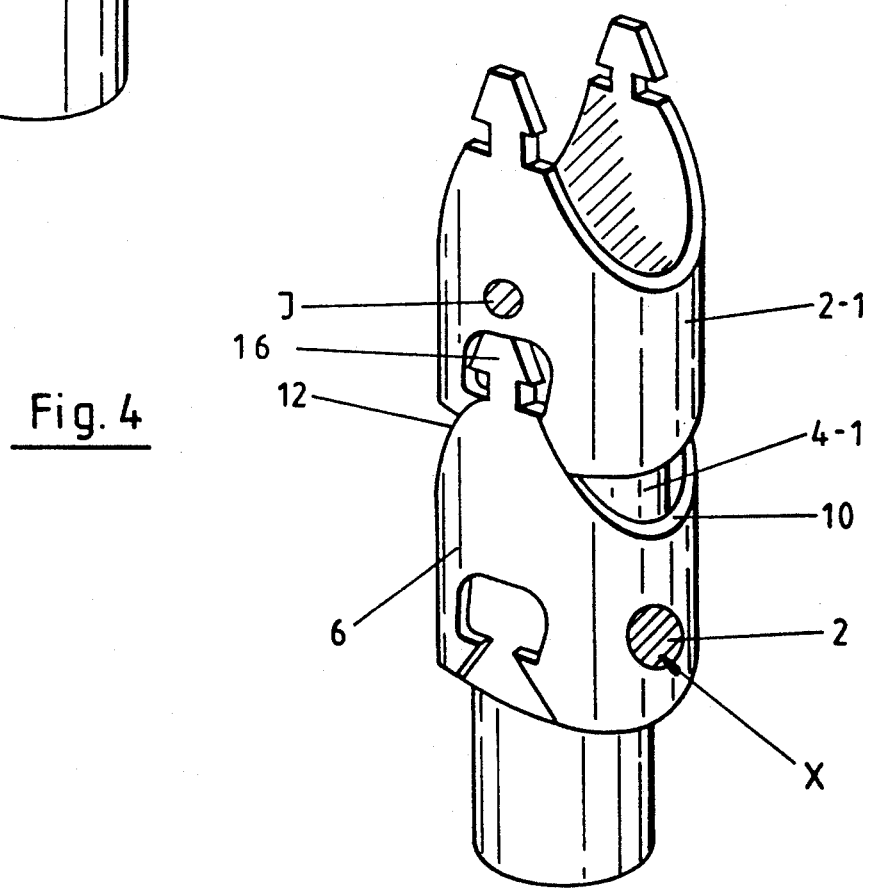
FIG. 4 shows a perspective view of the cuvettes according to FIGS. 2 and 3 in the fully inserted-into-each-other and locked state.

In the fitted-together state—as depicted in the FIG. 3—it is the chamfers 26,28 of the locking section 24 with the positioning surfaces 20,22 of the hook sections 16 which first come into bearing contact. With the aid of the wedge shape of the contact surfaces, a clean axial alignment of the insertionally fitted-together cuvettes takes place. In this relative positional relationship it is possible to form comparatively high stacks of cuvettes and, consequently, the latter can be accommodated in a cuvette dispenser, from which individual cuvettes are then taken out. The disposition is such that already in the relative position of the cuvettes 2, 2-1 as per FIG. 3, the measuring and stirring section 4-1 is fully inserted into the extension section 6 of the subjacent cuvette 2, whereby the measuring section or the volume of the measuring section holding the substrate to be analyzed is sealed from the outside. It is possible, therefore, to safely transport a stack of cuvettes in this relative position without running the risk that a stirring rod 8 already placed in the measuring section will fall out and possibly be lost and that the measuring windows, due to this fit, are unable to come into contact with the receiving cuvette, which prevents the scratching of the windows. It is from the stacked position depicted in the FIG. 3 that the measuring cuvettes 2, 2-1 can be individually filled with substrate to be analyzed subsequent to their having been placed into a measuring block or a mixing means or a rotor.

When it is intended to take the measuring cuvette out after the stirring operation or measuring operation has taken place, from the rotor or measuring block, an empty cuvette is slid on to the measuring cuvette so far that the hook sections 16 come into locking engagement with the locking sections 24 of the cuvette 2-1 placed thereupon. This state is shown in the FIG. 4. When the empty cuvette 2-1 is slid on, the sections 14 and, with them, the hook sections 16 yield radially outwardly, whereupon the hook sections 16 engage or latch behind the constriction 30 into the round portion 32 of the key hole-shaped recesses 24. In this case it can be seen that, by means of an appropriate construction of the chamfers 10,12 in adaptation to the sloping surfaces 26,28, a motion stop is provided so as to safeguard the hook sections 16 against excessive stresses. With the aid of the empty cuvette 2-1, which is preferably at the section 14, the measuring cuvette 2 can then be removed from the measuring block or from the rotor. The cuvette which had already been removed assumes the function of the empty cuvette during the next removing operation, whereby it is ensured that only one empty cuvette is necessary for the removal of the cuvettes. Since—as appears clearly from FIG. 4—the measuring and stirring section 4-1 of the empty cuvette 2-1 is inserted relatively far into the extension section 6 of the measuring cuvette 2, the chance of the measuring substrate escaping is very largely precluded, whereby the risk of contamination for the operator is kept as small as possible.

For the unlocking of the collar sections within the upper internal area of the hook sections can be constructed in such a way that they are provided with an undercut which makes it possible to grip behind the hooks 16 and to thus remove them from the retaining surfaces 24 and to thereby unlock the cuvette. This is possible, for instance, by seizing the measuring cuvette 2 at the points X—cf. FIG. 4—by means of thumb and index finger, so that the hook sections 16 move radially in the outward direction due to elastic radial deformation. In this condition the empty cuvette 2-1 can be pulled off from the cuvette 2 without any difficulty, i.e. without any force having to be used. Another possibility exists in compressing the sections 14 in the empty cuvette 2-1 at the points Y so that the hook sections, with their locking shoulders 18, are likewise brought out of alignment with the retaining surfaces 34 and, accordingly, an axial displacement of the two cuvettes 2, 2-1 relative to each other is rendered possible. It has been shown that already a very slight surface overlap between the retaining surfaces 34 and the locking shoulders 18 suffices in order to provide a sufficiently firm locking of the two cuvettes in the insertionally fitted-together state. Accordingly, already slight radial, elastic deformations of the two cuvettes relative to each other suffice for disengaging the hooking or locking or latching.

The concept of the cuvette construction described in the foregoing is generally realizeable for a large number of cuvette designs. It is true that special additional advantages result when the cuvette is constructed as has been individually illustrated in detail in the FIGS. 5 to 9. On this occasion identical reference numbers are used for those component parts of the cuvette which have already been employed with the aid of the FIGS. 1 to 4.

It can be seen from the illustrations as per FIGS. 5 to 9 that the cross-section of the measuring cuvette—see especially FIG. 9—has an oval or elliptical configuration diverging from the circular shape. This cross-sectional construction is provided both within the area of the extension section 6 as well as within the area of the measuring and stirring section 4. In particular within the area of the measuring and stirring section, this design has special advantages which will be described in greater detail below.

Round sections 40,42 adjoin continuously to plane parallel side wall sections 36,38 (cf. FIG. 7), which are e.g. formed by semicircle lines. It is true that, on this occasion, it would also be possible to make use of a parabolic configuration or of an elliptical section. In the connection with the plane or even construction of the bottom wall 44, good conditions resulted for the thorough mixing of the substrate held within the measuring space 46 by means of a stirring rod 8 or 48, which is shown in FIG. 8 in dot-dash lines in a somewhat modified form. Apart from this, between the plane parallel side walls 36,38 which are spaced apart from each other at a predetermined distance D and which possess a predetermined wall thickness W, a precisely defined measuring path or a reproducible measuring volume is provided, while the measuring layer thickness $D+2\times W$ provides the best conditions for a good reproducibility of photometric tests according to Lambert's Law. That is why the aforedescribed cuvette is quite particularly well suited for the analysis of chromogenic substrates and for photometric tests in the field of enzyme kinetics.

However, the prior condition for this is that the measuring section, at least within the area of the plane parallel side walls 36,38 is constructed so as to be highly transparent or clear. This is preferably achieved by the cuvette being comprised in its entirety of plastic of the group of the polystyrenes and polymethylacrylates. The use of polymethylacrylate has proved to be of particular advantage since this material is very clear or transparent and, in addition, can be formed with great accuracy, by way of example, it can be shaped in the injection moulding process or in the deep drawing process, respectively. It is possible in this connection to fabricate the cuvette from plastic which possesses an essentially uniform wall thickness within the range of 0.5 to 0.7 mm. In this case the layer thickness D lies within a range of between 5 and 10 mm. With the dimensions stated in the foregoing, with a height of the measuring section and of the extension section within a range of between 10 and 15 mm, an adequate elasticity of the cuvette sections is obtained so as to make it possible for them to be readily fitted together by reciprocal insertion and for separating them equally readily when in the insertionally fitted-together state.

The FIGS. 5 to 9 disclose that the extension section 6 passes into the actual measuring and stirring section 4 via an internal shoulder 50 or an external shoulder 52. In the fitted-together state of two cuvettes, the internal shoulder 50 may additionally be had recourse to for assisting in a sealing of the measuring space 46 from the outside. As becomes apparent in detail from FIG. 9, the internal contour 54 of the extension section 6 corresponds substantially to the external contour 56 of the measuring and stirring section 4, so that a positive engagement between the measuring cuvettes is ensured.

From FIG. 7 can be seen that the depth T of the recess 24 only constitutes a fraction of the wall thickness S of the extension section 6, which likewise lies within the range of between 0.5 and 0.7 mm. In order not to additionally weaken the hook sections 16, the same merge into the prismatic extension section 6 via step 58. The thickness W of the hook sections 16 can in this way be kept within the same order of magnitude as the wall thickness of the cuvette in the other part.

The inclination ALPHA of the chamfers 26,28 corresponds to the inclination BETA of the positioning surfaces 20,22 relative to the longitudinal center axis 60 of the cuvette. Also the angle GAMMA of the chamfers 10 and 12 is correspondingly selected.

In a departure from the aforedescribed embodiment example, it is also possible, in lieu of a one-piece construction of the cuvette, to fit two parts together by reciprocal insertion, viz. a measuring and a stirring section and an accommodation section adjoining thereto, it being necessary in this case, it is true, that it has to be ensured that the connection between said two parts is executed so as to be hermetically closed to the outside.

In the aforedescribed embodiment example the locking means are provided within the area of the extension section. This is not absolutely necessary. Rather, it is also possible to provide these locking means within the area of the measuring and stirring section, but preferably on the external surface.

It is also possible to provide additional locking aids within the area of the outer shoulder 52, e.g. in the form of bayonet-like closures.

The construction of the cuvette according to the invention also allows the combination of several cuvettes into assemblies or analysis arrays. This is diagrammatically indicated in the FIGS. 10 to 12. On this occasion the cuvettes are, for the sake of greater simplicity, depicted as having a cylindrical cross-section. It has to be emphasized, however, that also in such combinations of the cuvettes into measuring arrays, cross-sectional configurations can be employed as were explained with the aid of the FIGS. 1 to 9. In the arrangement according to the FIG. 10, measuring cuvettes 62 are combined into an annulus. For this purpose, at least the extension sections 66 are interconnected by means of preferably formed-on webs 67. The arrangement according to FIG. 10 may accordingly be inserted complete into a measuring block or into a rotor and be removed in its entirety by the superposition of a further identically constructed empty arrangement from the rotor or from the measuring block.

The embodiments according to the FIGS. 11 and 12 differ from the arrangement according to the FIG. 10 with regard to the number and the configuration of the arrangements. According to the FIG. 11, solely four measuring cuvettes 72 are combined into a segmental group while use is made of formed-on webs 77. By way of example, the centering angle DELTA is 90°.

The embodiment according to FIG. 12 differs from the one according to FIG. 11 merely in that here a linear disposition of the measuring cuvettes 82 is selected. The connecting webs are identified with 87.

Figure 13:
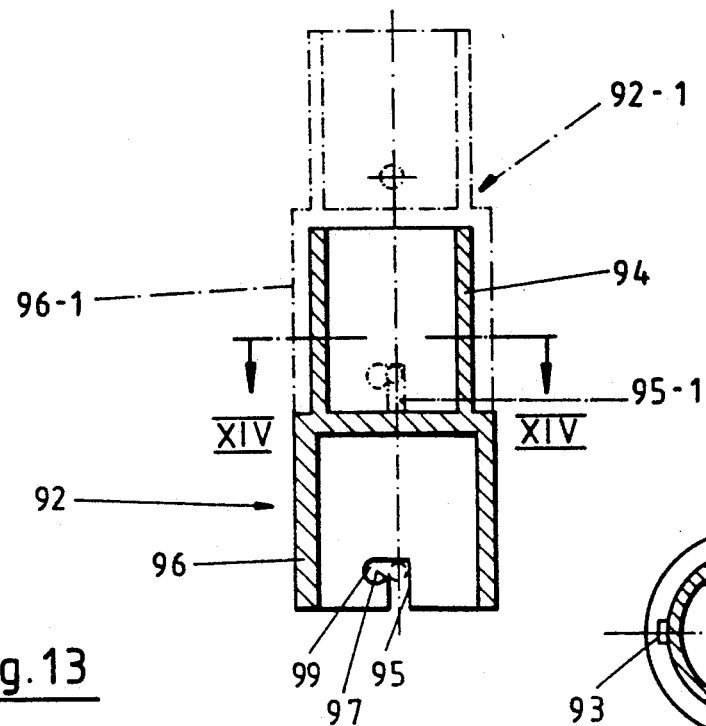
FIG. 13 shows a sectional view of a further embodiment of the measuring cuvette.
Figure 14:
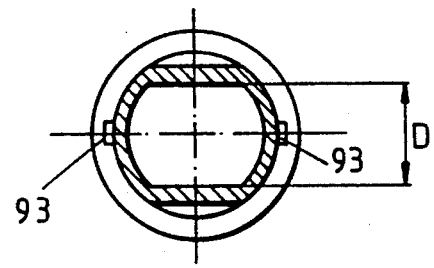
FIG. 14 shows a view of the section in the direction of XIV—XIV in FIG. 13.

In the FIGS. 13 and 14, a further embodiment of a measuring cuvette 82 is shown in which, in variation from the embodiment example previously described, the extension section 96 extends the measuring cuvette in the downward direction. The measuring and stirring section is identified with 94. According to this embodiment example, the measuring section 94 can be inserted into the extension section 96-1. In this case a knob 93 engages into a longitudinal slot 95-1 of the attached empty cuvette 92-1. In this position it is possible for the cuvettes to be stacked. By means of a relative twisting between the cuvettes, the knobs 93 latch via a constriction 97 into a slightly undercut recess 99, whereby a locking against being pulled off is established.

From the illustration according to FIG. 14 it can be seen that the plane parallel side walls of the measuring section 94 are also used in this embodiment, which, between themselves, define a layer cover of predetermined width D.

Figure 15:
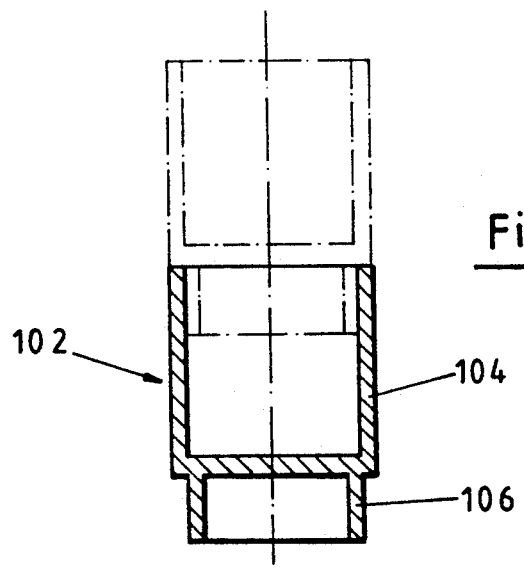
FIG. 15 shows a section of a further embodiment of the measuring cuvette.

Finally, with the aid of the FIG. 15, a third embodiment of a measuring cuvette 102 has to be described which differs from the previously described embodiments in that the measuring section 104 is constructed so as to be wider than the extension section 106, whose external contour in this embodiment corresponds to the internal contour of the measuring or stirring section 104. Here, too, a fitting together by reciprocal insertion is again possible, in which process lockings and latchings are employed which have not been depicted in any detail. By way of example, these may also be provided by a frictional connection between the internal surface of the section 104 and the external surface 106.

Figure 16:
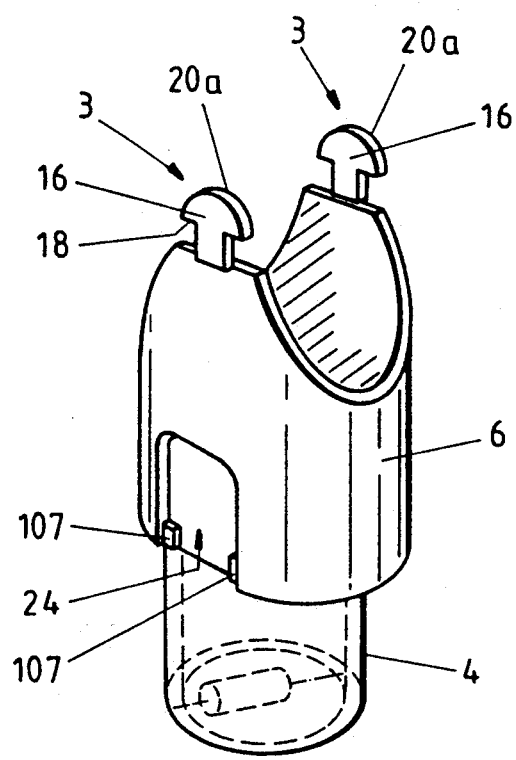
FIG. 16 shows, in a side elevation, a further embodiment of the measuring cuvette.

In the FIG. 16, a further embodiment of a cuvette is depicted, in which the locking parts 3 are constructed in the form of hook sections 16 which possess a positioning surface 20a in the form of a cylindrical section and two locking shoulders 18 each. On this occasion, too, the locking section 24 is constructed in the form of a recess or depression in the external surface of the extension section 6, provision is made, however, for at least one small projection 107 being constructed within the marginal area of each locking section 24, which has a smaller height than the depth of the locking section 24. It is possible hereby for the hook sections of a further, non-depicted cuvette to be inserted into the locking sections, in that they are pushed over the projections 107 and subsequently latch since the locking shoulders 18 of a hook section are then gripped from behind by the two projection 107 so that the two cuvettes are interconnected.

Figure 17:
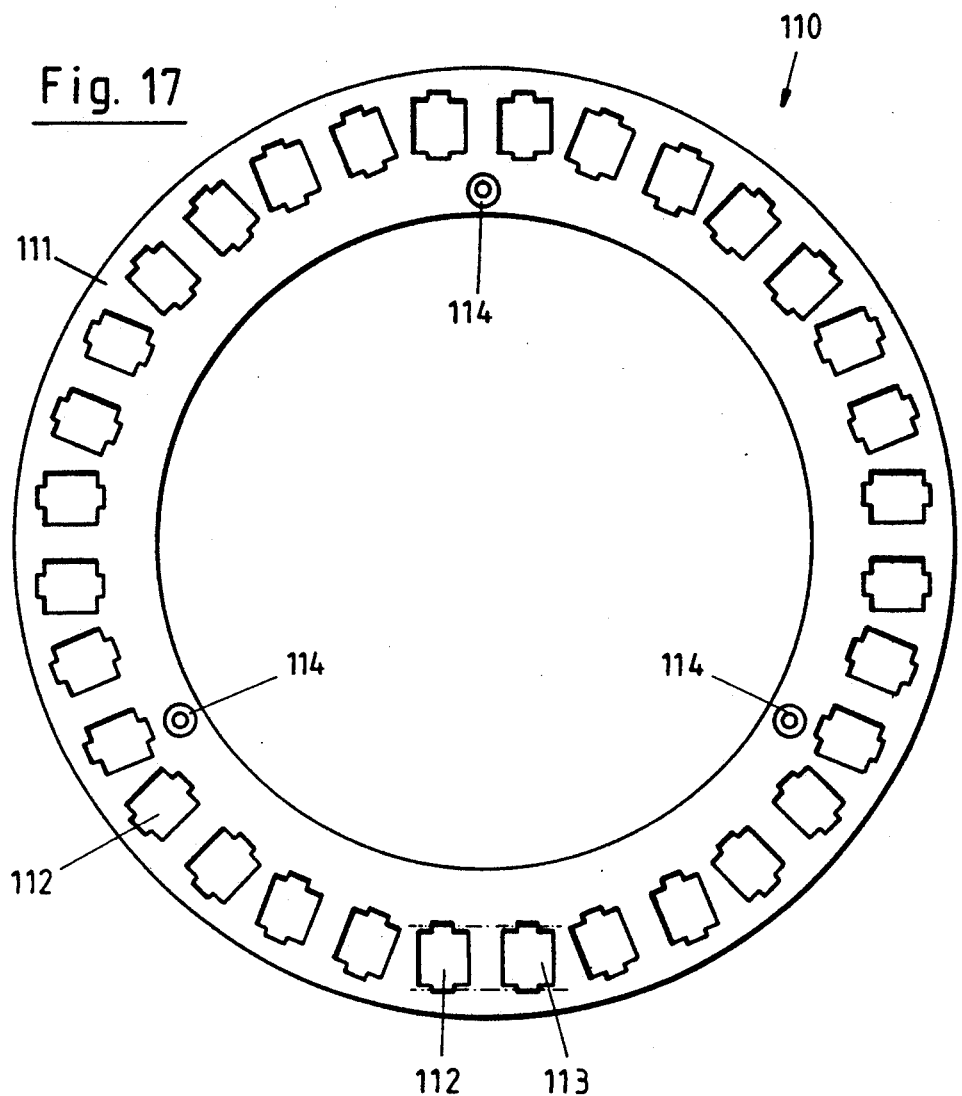
FIG. 17 shows, in a view from the top, a measuring rotor.
Figure 18:
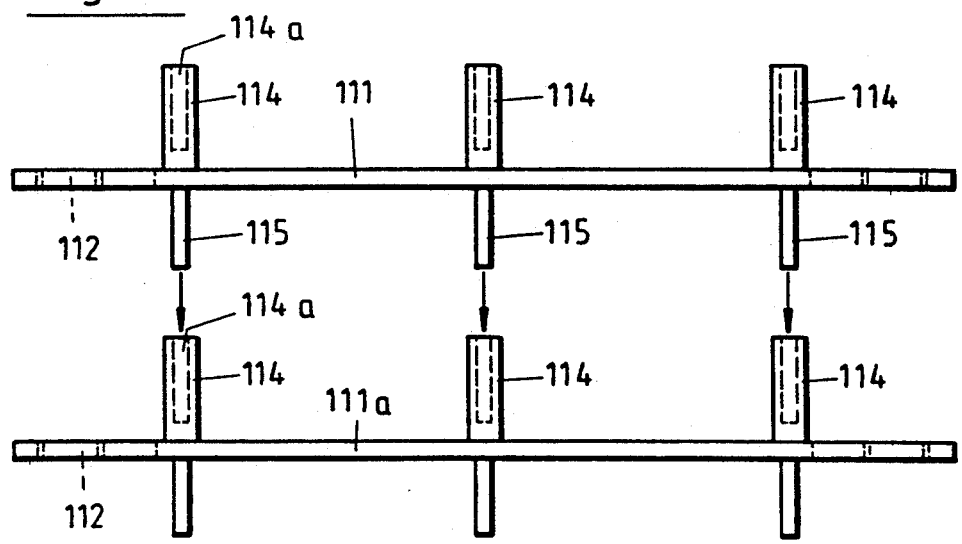
FIG. 18 shows, in a side elevation, two measuring rotors in the process of being placed on top of each other.

The measuring rotor 110 depicted in the FIGS. 17 and 18 is provided for use in automatic analyzers in which two measuring cuvettes are always simultaneously at a time. The measuring rotor 110 comprises in this case an annular disk 111, in which receiving perforations 112,113 are constructed. On account of the fact that the measuring disk is constructed in the form of an annular disk and that essentially equidistantly spaced-apart accommodation sections are constructed in the same, when cuvettes according to the invention are used, it can be equipped completely with cuvettes and especially also with the stirring member, in which case the measuring cuvettes can be secured with the aid of pertinently superimposed further measuring cuvettes.

In this case two receiving performations 112, 113 each are parallelly aligned, as is indicated in the drawing by the dashed line so that an arrangement of the measuring cuvettes is provided which is aligned the same way, it being made possible for them to be processed simultaneously in the analyzer. Furthermore, the measuring rotor 110 is provided, at the top and at the bottom, with interengaging guide elements which, in the stacked state, ensure that an appropriate distance is kept. The guide elements are constituted of receiving sleeves 114 disposed on one side in which a receiving bore 114a is provided and of inserting pins 115 correspondingly disposed on the other side of the measuring rotor. The disposition is effected in such a way that each inserting pin 115 is insertable into a receiving sleeve 114 of a further annular disk 111a. This possibility of stackability of the measuring rotors 111,11a does not only result in a ready stackability of the measuring rotors filled with corresponding measuring cuvettes, but, owing to the, at the same time, insertionally fittable-together measuring cuvettes, it leads to a securing of the mixing elements. In addition, on account of the circumstance that when the measuring rotors 11,111a are insertionally superimposed, the measuring cuvettes are inserted into each other (not depicted in the drawing), a securing of the mixing elements on the one hand and a protection of the measuring windows on the other is provided.

The rotor construction in this case is such that the receiving perforations are constructed in such a way that one cuvette at a time, with its measuring section, is insertable into a receiving perforation 112,113 and mountable by means of the extension section.

The interaction of the novel measuring cuvettes with the novel measuring rotor for the measuring cuvettes offers altogether great possibilities for a simplification of measurements with a, at the same time, very significantly increased safety in the handling of such measuring cuvettes.

I claim:

1. A cuvette for holding substances to be analyzed by optical means, and more particularly for the analysis of chromogenic substances, solutions or substrates, comprising:
    a measuring section, having a top and a bottom, and being closed at the bottom for holding the substance; and
    an extension section extending the cuvette and adjoining the measuring section, the extension section forming a detachable plug-in connection with the measuring section of a second cuvette.

2. A cuvette according to claim 1 wherein the extension section is coupled to the top of the measuring section and extends upwardly, wherein the extension section possesses an internal contour which corresponds substantially to an external contour of the measuring section.

3. A cuvette according to claim 2, wherein the extension section and the measuring section form a shoulder on the internal contour and/or on the external contour, and the cuvette and the second cuvette merge into each other via the shoulder.

4. A cuvette according to claim 1 wherein the extension section includes a first end and a second end, and is provided with at least one locking section which can be brought into locking engagement with a complementarily configured locking section on the second cuvette which is axially offset and aligned thereto on the second cuvette.

5. A cuvette according to claim 4 wherein the locking section is equipped with at least one positioning surface which, when joined with the second cuvette, can be brought into bearing contact with a corresponding positioning surface on the locking section of the second cuvette.

6. A cuvette according to claim 5, wherein the positioning surfaces of the first and second cuvettes are allocated to each locking section and taper towards each other in a wedge-shaped fashion.

7. A cuvette according to claim 4 wherein the extension section possesses several locking sections disposed spaced apart at a uniform circumferential distance.

8. A cuvette according to claim 7 wherein the locking sections possess axially aligned hook sections.

9. A cuvette according to claim 8 wherein the extension sections are formed of walls having a thickness and the hook sections have a thickness which corresponds substantially to the thickness of the cuvette within the extension section.

10. A cuvette according to claim 7 wherein the extension section further includes recesses in an external surface of the cuvette, wherein the recesses have a depth and a contour adapted to the configuration of at least one locking section.

11. A cuvette according to claim 10 wherein the cuvette is constructed so as to be radially elastic in at least the area of said at least one locking part and recess.

12. A cuvette according to claim 1 wherein the measuring section possesses an internal cross-section which diverges from the circular form.

13. A cuvette according to claim 12 wherein the measuring section includes two oppositely located, plane parallel, side wall sections of a predetermined thickness, which are spaced apart at a predetermined distance and which are connected by means of rounded portions.

14. A cuvette according to claim 13 wherein the predetermined thickness lies within the range of between 0.5 mm and 0.7 mm, and the predetermined distance of the plane parallel side wall sections is about between 5 mm and 10 mm.

15. A cuvette according to claim 13 wherein the cuvette includes two locking sections which are aligned in the axial direction with the respective side wall sections.

16. A cuvette according to claim 1 wherein the measuring section of the cuvette is inserted into the extension section of the second cuvette and comes to lie completely within the extension section, such that the measuring section of the first cuvette is stored in a scratch-proof manner, can be transported in a scratch-proof manner, and can be individually introduced into a measuring device.

17. A cuvette according to claim 1 wherein the measuring section and the extension section are interconnected so as to constitute one piece.

18. A cuvette according to claim 1 wherein the cuvette, is comprised of clear plastic.

19. A cuvette according to claim 18 wherein the plastic is selected from the group of polystyrenes and polymethylacrylates.

20. A cuvette according to claim 19 wherein the plastic is selected from the group of the polymethylmethacrylates (PNMA).

21. A cuvette according to claims 1 wherein the bottom of the measuring section is constructed so as to be even and planar.

22. A cuvette arrangement according to claim 1 wherein the extension section includes two opposing surfaces constructed on a projection, the extension section having locking shoulders formed therein, the projection being insertable into the locking shoulders of the second cuvette such that the projection grips behind the locking shoulders of the second cuvette.

23. A cuvette according to claim 1 wherein the extension section includes a locking section, the locking section includes at least one projection, the projection including a cam having a smaller height than the depth of a recess section formed in the extension section, so that the hook section of the second cuvette can be pushed over the cam and grip behind a locking shoulder of the recess section and retain the second cuvette.

24. An arrangement of cuvettes, each of the cuvettes for holding a substance to be measured, comprising:
a plurality of cuvettes, each including
a measuring section having a top and a bottom, being closed at the bottom for holding the substance;
an extension section coupled to the top of the measuring section, the extension section including a locking section for forming a detachable, plug-in connection with a measuring section of a second cuvette; and
a plurality of webs formed on the extension section of the cuvettes, interconnecting the cuvettes.

25. The arrangement of several cuvettes according to claim 23 wherein the cuvettes are interconnected by the webs to form a arcuate, semi-circular arrangement.

26. An arrangement according to claim 25, wherein the cuvettes are disposed in a circle.

27. An arrangement according to claim 24 wherein the plurality of cuvettes are disposed in a series so as to form a linear strip of cuvettes.

28. An arrangement of cuvettes, comprising:
a plurality of cuvettes, each including
a measuring section having a top and a bottom, being closed at the bottom for holding the substance, and
an extension section coupled to the top of the measuring section, the extension section including a locking section for forming a detachable, plug-in connection with a measuring section of a second cuvette; and
a rotor constructed in the form of an annular disk having receiving perforations, each of the cuvettes being insertable into a receiving perforation and mountable with the aid of the extension section.

29. An arrangement according to claim 28, wherein at least two of the receiving perforations are disposed so as to be parallel.

30. An arrangement according to claim 29, wherein the annular disk includes a top side provided with at least one receiving sleeve and, an underside with at least one inserting pin, the inserting pin being insertable into a receiving sleeve of a second annular disk.

* * * * *

UNITED STATES PATENT AND TRADEMARK OFFICE
CERTIFICATE OF CORRECTION

PATENT NO. : 5,285,253

DATED : February 8, 1994

INVENTOR(S) : Bernd Kloth

It is certified that error appears in the above-identified patent and that said Letters Patent is hereby corrected as shown below:

Col. 3, line 40: "arew" should be "are"

Col. 7, line 51: "construction" should be "constriction"

Col. 11, line 53: "projection" should be "projections"

Col. 11, line 57: between "always" and "simultaneously" insert --used--

Col. 12, line 1: "performations" should be "perforations"

Col. 12, line 17: "111,11a" should be "111,111a"

Col. 12, line 23: "11,111a" should be "111,111a"

Col. 14, line 3: "(PNMA)" should be "(PMMA)"

Col. 14, line 4: "claims" should be "claim"

UNITED STATES PATENT AND TRADEMARK OFFICE
CERTIFICATE OF CORRECTION

PATENT NO. : 5,285,253

DATED : February 8, 1994

INVENTOR(S) : Bernd Kloth

It is certified that error appears in the above-identified patent and that said Letters Patent is hereby corrected as shown below:

Col. 14, line 37: "a" should be "an"

Col. 14, line 47: after "stance" delete ", and" and insert a semicolon

Signed and Sealed this

Twentieth Day of December, 1994

Attest:

BRUCE LEHMAN

*Attesting Officer*  *Commissioner of Patents and Trademarks*